United States Patent
Bagui et al.

(10) Patent No.: US 9,611,345 B2
(45) Date of Patent: Apr. 4, 2017

(54) TRANSITION METAL BASED PRO-CATALYST AND A PROCESS FOR ITS PREPARATION

(71) Applicant: RELIANCE INDUSTRIES LIMITED, Maharashtra (IN)

(72) Inventors: Mahuya Bagui, Gujarat (IN); Yogesh Popatrao Patil, Gujarat (IN); Viralkumar Patel, Gujarat (IN); Krishna Renganath Sarma, Gujarat (IN); Raksh Vir Jasra, Gujarat (IN); Ajit Behari Mathur, Gujarat (IN); Suketu Vakil, Maharashtra (IN)

(73) Assignee: RELIANCE INDUSTRIES LIMITED (IN)

(*) Notice: Subject to any disclaimer, the term of this patent is extended or adjusted under 35 U.S.C. 154(b) by 0 days.

(21) Appl. No.: 14/785,306

(22) PCT Filed: Apr. 15, 2014

(86) PCT No.: PCT/IN2014/000234
§ 371 (c)(1),
(2) Date: Oct. 16, 2015

(87) PCT Pub. No.: WO2014/170913
PCT Pub. Date: Oct. 23, 2014

(65) Prior Publication Data
US 2016/0108146 A1 Apr. 21, 2016

(30) Foreign Application Priority Data
Apr. 17, 2013 (IN) .................. 1440/MUM/2013

(51) Int. Cl.
| | | |
|---|---|---|
| *C08F 4/76* | (2006.01) | |
| *C08F 4/64* | (2006.01) | |
| *C08F 110/02* | (2006.01) | |
| *C07F 7/00* | (2006.01) | |
| *B01J 31/22* | (2006.01) | |
| *C07F 7/28* | (2006.01) | |

(52) U.S. Cl.
CPC ......... *C08F 110/02* (2013.01); *B01J 31/2243* (2013.01); *C07F 7/006* (2013.01); *C07F 7/28* (2013.01); *B01J 2531/0252* (2013.01); *B01J 2531/46* (2013.01); *B01J 2531/49* (2013.01); *B01J 2531/56* (2013.01); *B01J 2531/57* (2013.01); *B01J 2531/58* (2013.01); *B01J 2531/66* (2013.01); *B01J 2531/72* (2013.01); *B01J 2531/74* (2013.01); *B01J 2531/842* (2013.01)

(58) Field of Classification Search
CPC .... C08F 4/62189; C08F 4/60189; C08F 4/76; C08F 10/02; C08F 2500/01; C07F 7/28
See application file for complete search history.

(56) References Cited

U.S. PATENT DOCUMENTS

| | | | |
|---|---|---|---|
| 5,637,739 A | 6/1997 | Jacobsen et al. | |
| 6,309,997 B1* | 10/2001 | Fujita | C07F 7/006 502/103 |
| 9,175,108 B2* | 11/2015 | Sarma | C08F 10/02 |
| 2010/0144224 A1* | 6/2010 | De Weijer | B29C 55/005 442/1 |
| 2011/0162517 A1* | 7/2011 | Bovenschen | F41H 5/0485 89/36.02 |

FOREIGN PATENT DOCUMENTS

| | | | | |
|---|---|---|---|---|
| CN | 1251842 A | * | 5/2000 | ................ C08F 4/76 |
| CN | 1315460 A | * | 10/2001 | .............. C08F 10/00 |

(Continued)

OTHER PUBLICATIONS

Huang et al. Chinese Journal of Chemistry 2004, 22, 577-584.*
Huang et al. Inorg. Chem. Commun. 2001, 4, 392-394.*
Morris et al. Inorg. Chem. 2001, 40, 3222-3227.*
Salavati-Niasari et al. J. Mol. Catal. A; Chemical 2007, 261, 147-155.*
ISA/Indian Patent Office International Search Report and Written Opinion for International Application No. PCT/IN2014/000234, Nov. 24, 2014, 3 pages.
Bialek et al., Transition Metal Complexes of Tetradentate and Bidentate Schiff Bases as Catalysts for Ethylene Polymerization: Effect of Transition Metal and Cocatalyst, Journal of Polymer Science: Part A: Polymer Chemistry, vol. 47, pp. 565-575, Oct. 24, 2008.

(Continued)

*Primary Examiner* — Rip A Lee
(74) *Attorney, Agent, or Firm* — Fish & Tsang, LLP (57) ABSTRACT

The present disclosure relates to a transition metal based pro-catalyst represented by Formula I: wherein, the substituents have the meaning as defined in the specification. The present disclosure also relates to a process for preparing the transition metal based pro-catalyst represented by Formula I and the catalyst composition obtained therefrom. Further, the present disclosure relates to a process for polymerizing olefins by employing the catalyst composition comprising the transition metal based pro-catalyst represented by Formula I.

18 Claims, 4 Drawing Sheets

Formula I (56) References Cited

FOREIGN PATENT DOCUMENTS

| CN | 101089006 A | 12/2007 |
|---|---|---|
| CN | 101280031 A | 10/2008 |
| CN | 101659628 A | 3/2010 |
| CN | 102936301 A | 2/2013 |
| WO | WO 2013/076733 A2 * | 5/2013 |
| WO | 2013118140 A2 | 8/2013 |

OTHER PUBLICATIONS

Chen et al., Arene-Bridged Salicylaldimine-Based Binuclear Neutral Nickel(II) Complexes: Synthesis and Ethylene Polymerization Activities, Organometallics, China, vol. 26, pp. 617-625, Aug. 26, 2006.

Terunori Fujita, FI Catalysts for Olefin Oligomerization and Polymerization: Principles and Practice, Mitsui Chemical Singapore R&D Center, Pte. Ltd., Singapore, pp. 1-2, Downloaded on Oct. 15, 2015.

Furuyama et al., Ethylene and propylene polymerization behavior of a series of bis(phenoxy—imine)titanium complexes, Journal of Molecular Catalysis A: Chemical 200, pp. 31-42, Jan. 18, 2003.

* cited by examiner

TRANSITION METAL BASED PRO-CATALYST AND A PROCESS FOR ITS PREPARATION

FIELD OF DISCLOSURE

The present disclosure relates to a pro-catalyst and a process for the preparation of the same. The present disclosure also relates to use of the said pro-catalyst for polymerization reactions.

BACKGROUND

High molecular weight polyolefins possess physical properties such as high abrasion resistance, high impact strength and low coefficient of friction. Therefore, high molecular weight polyolefins in various forms such as fibre, sheet, bio-material, wire and cable are in high demand. Polyolefins with molecular weight higher than one million g/mol, usually referred to as Ultra-high Molecular Weight Polyolefins are gaining popularity for versatile applications in various areas ranging from bio-medicals to ballistic materials. Ultra High Molecular Weight Polyethylene wherein the polymer chains are least entangled (maximum disentanglement of chains) exhibits porous morphology, high crystallinity and interesting solid state applications below melt temperature, which makes it suitable for biomedical applications such as polymeric supports in the three-dimensional regeneration and substitution of tissues by artificial prosthesis, besides applications in defence, requiring high impact strength.

Polyolefins are known to be manufactured using transition metal-catalysed polymerization technology. Typically, the catalysts used in manufacturing polyolefins are usually multi-site heterogeneous Ziegler-Natta catalysts. With the advancement in polymerization technology, single-site catalysts or group (IV) metallocene catalysts are increasingly being used for manufacturing polyolefins. Single-site catalysts and metallocene catalysts are continuously being designed to suit vital manufacturing process requirements. The improvement in the catalyst is carried out to achieve zero or near zero fouling of the equipment used and maintain catalyst activity. Development of such a catalyst with composite capability to impart various desired properties to the final product requires a careful selection of catalyst complex. Further, the selection of an appropriate ligand to be complexed with the metal component of the catalyst is carried out in such a manner that it imparts intended properties to the final product.

For instance, ethylene polymerization reaction catalysed by homogeneous single-site catalyst involves electron exchange between a ligand and a metal. It has been reported in literature that the ligand structure plays a role in determining the activity as well as the stereo-specificity of catalysts. By nature, ligands are electronically flexible and thus fulfil the requirement of imparting high activity to a resulting catalyst complex besides tailoring the same for achieving desired molecular weight, porosity, morphology, bulk density and high crystallinity of the resultant polymer.

Continuous research has resulted in the discovery of a number of highly active catalysts for the polymerization of ethylene, which include phenoxy-imine ligand early transition metal complexes (FI catalysts), pyrrolide-imine ligand group IV transition metal complexes (PI catalysts), indolide-imine ligand Ti complexes (II catalysts), phenoxy-imine ligand group (IV) transition metal complexes (IF catalysts), phenoxy-ether ligand Ti complexes (FE catalysts), imine-pyridine ligand late transition metal complexes (IP catalysts), and tris(pyrazolyl)borate ligand Ta complexes (PB catalysts). Some of the prior arts are discussed herein below.

CN101280031 discloses a process for preparing catalyst system comprising a 5,5-isopropylidene-bis (3-tert-butyl-hydroxybenzaldehyde)imine ligand complexed with transition metal. The catalyst system is prepared by reacting 5,5-isopropylidene-bis(3-tert-butyl-hydroxybenzaldehyde) with mono-amine to obtain a ligand which is then complexed with a transition metal compound.

CN101089006 discloses nickel based salicylaldehyde bridged binuclear carbodiimide type compound. The nickel based catalyst disclosed in CN101089006 when used for polymerization reaction result in ethylene oligomers and polymer with molecular weight in the range limited up to 1 lakh only.

An article titled "Arene-bridged salicylaldimine-based binuclear neutral Nickel(II) complexes: Synthesis and ethylene polymerization activities" published in Organometallics 2007, 26, 617-625 discloses nickel based catalyst having [O,N]-type ligand.

Another article titled "Ethylene and propylene polymerization behaviour of a series of bis(phenoxy-imine)titanium complexes" authored by Rieko Furuyama et al, published in Journal of Molecular Catalysis A: Chemical 200 (2003) 31-42, discloses titanium based catalysts for polymerization of ethylene and propylene. The ligand obtained by reacting 3-t-butyl salicyaldehyde/3,5-di-t-butyl salicyaldehyde and mono-amine is complexed with titanium halide to prepare the catalyst.

Still another article titled "Transition Metal Complexes of Tetradentate and Bidentate Schiff bases as Catalysts for Ethylene Polymerization: Effect of Transition Metal and Cocatalyst." authored by Marzena Bialek, et al, published in Journal of Polymer Science: Part A: Polymer Chemistry, Vol. 47, 565-575 (2009) discloses catalyst based on transition metals such as vanadium. titanium and zirconium. The ligand complex of the catalyst is prepared by reacting ortho-phenylene diamine and salicyaldehyde which is then complexed with transition metal to obtain the catalyst.

WO2013118140 disclose chemically immobilized heterogeneous polymerization catalyst having a salicylaldehyde imine ligand complexed with transition metal compound which is supported by a functionalized inorganic support.

The article titled "A Novel Catalyst for Olefin Polymerization" by Prof. Dr. Ibrahim M. Al Najjar, published in The Saudi International Petrochemical Technologies Conference, 2011, discloses a transition metal based catalyst which employs para-phenylene diamine for the preparation of the ligand complex.

FI catalysts are also disclosed in an article titled FI Catalysts for Olefin Oligomerization and Polymerization Principles and Practice authored by Terunori Fujita Some of the prior art catalysts are less efficient for polymerizing olefins to achieve polymers having molecular weight in the range of 1 million g/mole. Further, the rapid reaction kinetics profile exhibited by the catalysts known in the prior art under ambient temperature and high pressure, in conjunction with the living nature of some of the catalysts has posed a challenge in regulating the molecular weight of the polymer. The problem of regulating molecular weight is further aggravated in obtaining polymers having lower molecular weight in the range of 1 million g/mol to 6 million g/mol due to uncontrollable reaction kinetics. It generally increases reaction temperature much above 65° C. which if not pacified effectively leads to formation of polymer lumps in the reaction mass. This finally ends up with fouling of the polymerization unit. Thus, eventually use of catalysts known in the prior art lead to increase in the operational cost for polymerization process due to need of frequent maintenance.

Therefore, there exists a need to develop a catalyst for polymerization reactions with improved reaction kinetic control, least operational cost and molecular weight regulation properties.

OBJECTS

Some of the objects of the present disclosure are discussed herein below.

It is an object of the present disclosure to ameliorate one or more problems of the prior art or to at least provide a useful alternative.

It is another object of the present disclosure to provide a transition metal based pro-catalyst.

It is still another object of the present disclosure to provide a transition metal based pro-catalyst for polymerization of olefins to produce polyolefins having ultra-high molecular weight.

It is yet another object of the present disclosure to provide a transition metal based pro-catalyst having improved reaction kinetic control leading to controlled molecular weight of the polymer.

It is still another object of the present disclosure to provide a transition metal based pro-catalyst with improved reaction kinetic control to obviate the fouling of the polymerization unit.

It is yet another object of the present disclosure to provide a process for preparing a transition metal based pro-catalyst which is simple and economic.

It is still another object of the present disclosure to provide a process for polymerizing olefins that employs a transition metal based pro-catalyst.

It is still another object of the present disclosure to provide a pro-catalyst suitable for both heterogeneous and homogeneous polymerization processes.

It is further object of the present disclosure to provide a catalyst composition comprising the pro-catalyst.

Other objects and advantages of the present disclosure will be more apparent from the following description which is not intended to limit the scope of the present disclosure.

SUMMARY

In one aspect of the present disclosure there is provided a transition metal based pro-catalyst represented by Formula I:

a.

b. Formula I wherein, $R^1$, $R^2$, $R^4$, $R^6$ $R^8$, $R^{10}$ and $R^{12}$ are same or different, and independently selected from the group consisting of hydrogen, aryl, hetero-aryl and halide;

$R^5$ and $R^9$ are tertiary alkyl groups;

$R^7$ and $R^{11}$ are same or different, and independently selected from the group consisting of hydrogen and tertiary alkyl group;

$R^3$ is independently selected from the group consisting of hydrogen, halogen, alkoxy, aryloxy, carboxylic and sulphonic;

M is a transition metal selected from the group consisting of Hafnium (Hf), Manganese (Mn), Iron (Fe), Rhenium (Re), Tungsten (W), Niobium (Nb), Tantalum (Ta), Vanadium (V) and Titanium (Ti);

X is a halide selected from the group consisting of Cl, Br and I; and n is an integer 2.

Typically, the said pro-catalyst consists of a set of substituents selected from the group consisting of:

i. $R^1$, $R^2$, $R^3$, $R^4$, $R^6$, $R^7$, $R_8$, $R^{10}$, $R^{11}$ and $R^{12}$ being hydrogen; $R^5$ and $R^9$ being tertiary butyl groups; M is Titanium (Ti); X is Cl and n is an integer 2; and ii. $R^1$, $R^2$, $R^3$, $R^4$, $R^6$, $R^8$, $R^{10}$ and $R^{12}$ being hydrogen; $R^5$, $R^9$, $R^7$ and $R^{11}$ being tertiary butyl groups; M is Titanium (Ti); X is Cl and n is an integer 2.

In accordance with another aspect of the present disclosure there is provided a process for preparing the transition metal based pro-catalyst, said process comprising:

iii. reacting aromatic diamine of Formula (II) and at least one substituted salicylaldehyde of Formula (IIIa/IIIb) to obtain a Schiff base imine ligand of Formula (IV), Formula (II)

Formula (IIIa)

Formula (IIIb)

-continued

Formula (IV)

wherein, $R^1$, $R^2$, $R^4$, $R^6$ $R^8$, $R^{10}$ and $R^{12}$ are same or different, and independently selected from the group consisting of hydrogen, aryl, hetero-aryl and halide;
$R^5$ and $R^9$ are tertiary alkyl groups;
$R^7$ and $R^{11}$ are same or different, and independently selected from the group consisting of hydrogen and tertiary alkyl group;
$R^3$ is independently selected from the group consisting of hydrogen, halogen, alkoxy, aryloxy, carboxylic and sulphonic, and iv. optionally; introducing an alkali metal ion in the Schiff base imine ligand of Formula (IV) using an alkali metal ion introducing agent to obtain an alkali metal salt of Schiff base imine ligand of Formula (V), and

Formula (IV)

Formula (V)

wherein, $R^1$, $R^2$, $R^4$, $R^6$ $R^8$, $R^{10}$ and $R^{12}$ are same or different, and independently selected from the group consisting of hydrogen, aryl, hetero-aryl and halide;
$R^5$ and $R^9$ are tertiary alkyl groups;
$R^7$ and $R^{11}$ are same or different, and independently selected from the group consisting of hydrogen and tertiary alkyl group;
$R^3$ is independently selected from the group consisting of hydrogen, halogen, alkoxy, aryloxy, carboxylic and sulphonic; and
$M_1$ is an alkali metal ion of alkali metal ion introducing agent, and v. chelating the Schiff base imine ligand of Formula IV or alkali metal salt of Schiff base imine ligand of Formula (V) with the transition metal halide to obtain the transition metal based pro-catalyst represented by Formula I:

Formula I wherein, $R^1$, $R^2$, $R^4$, $R^6$ $R^8$, $R^{10}$ and $R^{12}$ are same or different, and independently selected from the group consisting of hydrogen, aryl, hetero-aryl and halide;
$R^5$ and $R^9$ are tertiary alkyl groups;
$R^7$ and $R^{11}$ are same or different, and independently selected from the group consisting of hydrogen and tertiary alkyl group;
$R^3$ is independently selected from the group consisting of hydrogen, halogen, alkoxy, aryloxy, carboxylic and sulphonic;
M is a transition metal selected from the group consisting of Hafnium (Hf), Manganese (Mn), Iron (Fe), Rhenium (Re), Tungsten (W), Niobium (Nb), Tantalum (Ta), Vanadium (V) and Titanium (Ti);
X is a halide selected from the group consisting of Cl, Br and I; and
n is an integer 2.

Typically, the ratio of Schiff base imine ligand of Formula IV or alkali metal salt of Schiff base imine ligand of Formula (V) to the transition metal halide is 1:1.

Typically, the step (i) is carried out in the presence of at least one compound selected from the group consisting of p-toluene sulfonic acid and sulphuric acid in at least one liquid medium selected from the group consisting of toluene, xylene, hexane, methanol and ethanol at a temperature ranging from 40° C. to the boiling point of the liquid medium.

Typically, the substituted salicylaldehyde is at least one compound selected from the group consisting of 3-tert-butyl salicylaldehyde and 3,5-di-tert-butyl salicylaldehyde.

Typically, the substituted salicylaldehyde of Formula (IIIa) and the substituted salicylaldehyde of Formula (IIIb) are same or different.

Typically, the said pro-catalyst consists of a set of substituents selected from the group-consisting of:

$R^1$, $R^2$, $R^3$, $R^4$, $R^6$, $R^7$, $R^8$, $R^{10}$, $R^{11}$ and $R^{12}$ being hydrogen; $R^5$ and $R^9$ being tertiary butyl groups; M is Titanium (Ti); X is Cl; and n is an integer 2; and $R^1$, $R^2$, $R^3$, $R^4$, $R^6$, $R^8$, $R^{10}$ and $R^{12}$ being hydrogen; $R^5$, $R^9$, $R^7$ and $R^{11}$ being tertiary butyl groups; M is Titanium (Ti); X is Cl; and n is an integer 2.

Typically, the alkali metal ion introducing agent is at least one selected form the group consisting of n-butyl lithium, sodium hydride, lithium aminoalkoxide and lithium diisopropylamide.

In accordance with yet another aspect of the present disclosure there is provided a catalyst composition comprising:

a. a transition metal based pro-catalyst represented by Formula I;

Formula I wherein, $R^1$, $R^2$, $R^4$, $R^6$ $R^8$, $R^{10}$ and $R^{12}$ are same or different, and independently selected from the group consisting of hydrogen, aryl, hetero-aryl and halide;

$R^5$ and $R^9$ are tertiary alkyl groups;

$R^7$ and $R^{11}$ are same or different, and independently selected from the group consisting of hydrogen and tertiary alkyl group;

$R^3$ is independently selected from the group consisting of hydrogen, halogen, alkoxy, aryloxy, carboxylic and sulphonic;

M is a transition metal selected from the group consisting of Hafnium (Hf), Manganese (Mn), Iron (Fe), Rhenium (Re), Tungsten (W), Niobium (Nb), Tantalum (Ta), Vanadium (V) and Titanium (Ti);

X is a halide selected from the group consisting of Cl, Br and I; and n is an integer 2, b. at least one alkyl aluminium co-catalyst; and c. at least one inert hydrocarbon liquid medium.

Typically, the alkyl aluminium co-catalyst is at least one compound selected from the group consisting of methylaluminoxane, poly-methylaluminoxane, triethyl aluminium, isoprenyl aluminium, aluminium sesquichloride, tri-n-octyl aluminium and triisobutyl aluminium.

In one embodiment of the present disclosure the co-catalyst is polymethyl aluminoxane.

Typically, the ratio of elemental aluminium to elemental titanium (Al/Ti) is in the range of 50:1 to 1000:1.

Typically, the inert hydrocarbon liquid medium is at least one selected from the group consisting of pentane, hexane, cyclohexane, methyl cyclohexane, heptane, octane, decane, toluene, isopentane and varsol.

In one embodiment of the present disclosure the ratio of elemental aluminium to elemental titanium (Al/Ti) is in the range of 200:1 to 300:1 and the inert hydrocarbon liquid medium is varsol.

In accordance with yet another aspect of the present disclosure there is provided a process for polymerizing olefin, said process comprising:

i. mixing the transition metal based pro-catalyst of claim 1 and at least one co-catalyst in a proportion wherein the ratio of elemental aluminium to elemental titanium ranges from 50:1 to 1000:1, in the presence of at least one inert hydrocarbon liquid medium at a temperature ranging from 10° C. to 30° C. to obtain an activated catalyst composition, ii. adding at least one olefin monomer to the activated catalyst composition to obtain a reaction mixture, and iii. subjecting the reaction mixture to the polymerization at a temperature ranging from −5° C. to 70° C., and a pressure ranging from 0.1 to 11 bars for a time period ranging from 1 hour to 10 hours to obtain the polymerized olefin.

In accordance with yet another aspect of the present disclosure there is provided a polyolefin obtained by the process as described herein above, wherein said polyolefin is dis-entangled ultra-high molecular weight and characterized by at least one of the following properties:

vi. a bulk density in the range of 0.05 to 0.1 g/cc;

vii. a molecular weight in the range of 1 million g/mole to 6 million g/mole;

viii. crystallinity in the range of 90 to 99%;

ix. intrinsic viscosity in the range of 10 to 32 dl/g; and x. fibrous and porous morphology.

Typically, the inert hydrocarbon liquid medium is at least one selected from the group consisting of pentane, hexane, cyclohexane, methyl cyclohexane, heptane, octane, decane, toluene, isopentane and varsol.

In one embodiment of the present disclosure the olefin monomer is ethylene and the inert hydrocarbon liquid medium is varsol.

DETAILED DESCRIPTION

In accordance with one aspect of the present disclosure there is provided a transition metal based pro-catalyst which can be employed for the polymerization of olefins to prepare dis-entangled ultra-high molecular weight polyolefins.

The novel transition metal based pro-catalyst of the present disclosure is represented by Formula I:

c.

d. Formula I $R^1$, $R^2$, $R^4$, $R^6$ $R^8$, $R^{10}$ and $R^{12}$ which are the substituents in Formula I are same or different, and independently selected from the group consisting of hydrogen, aryl, hetero-aryl and halide. The substituents $R^5$ and $R^7$ in Formula I are tertiary alkyl groups, whereas $R^7$ and $R^{11}$ are same or different, and independently selected from the group consisting of hydrogen and tertiary alkyl group.

Further, $R^3$ is selected from the group consisting of hydrogen, halogen, alkoxy, aryloxy, carboxylic and sulphonic.

"M" in the Formula I is a transition metal selected from the group consisting of Hafnium (Hf), Manganese (Mn), Iron (Fe), Rhenium (Re), Tungsten (W), Niobium (Nb), Tantalum (Ta), Vanadium (V) and Titanium (Ti) whereas X is a halide selected from the group consisting of Cl, Br and I.

n in the Formula I is the number of X ions satisfying the valency of the transition metal ion and is 2.

In one embodiment the substituents in Formula (I) are as follows:

$R^1$, $R^2$, $R^3$, $R^4$, $R^6$, $R^7$, $R^8$, $R^{10}$, $R^{11}$ and $R^{12}$ being hydrogen; $R^5$ and $R^9$ being tertiary butyl groups; M is Titanium (Ti); X is Cl and n is an integer 2.

In another embodiment the substituents in Formula (I) are defined as follows:

$R^1$, $R^2$, $R^3$, $R^4$, $R^6$, $R^8$, $R^{10}$ and $R^{12}$ being hydrogen; $R^5$, $R^9$, $R^7$ and $R^{11}$ being tertiary butyl groups; M is Titanium (Ti); X is Cl and n is an integer 2.

In accordance with another aspect of the present disclosure there is provided a process for preparing a transition metal based pro-catalyst of Formula (I).

The process for preparing a transition metal based pro-catalyst of the present disclosure is described herein after.

In the first step, an aromatic diamine of Formula (II) and at least one substituted salicylaldehyde of Formula (IIIa/IIIb) is reacted to obtain a Schiff base imine ligand of Formula (IV). The reaction is carried out in the presence of at least one compound selected from the group consisting of p-toluene sulfonic acid and sulphuric acid in at least one liquid medium selected from the group consisting of toluene, xylene, hexane, methanol and ethanol at a temperature ranging from 40° C. to the boiling point of the liquid medium.

The reaction is represented schematically as below.

The substituents in Formulas II, IIIa, IIIb and IV are defined as:

$R^1$, $R^2$, $R^4$, $R^6$ $R^8$, $R^{10}$ and $R^{12}$ are same or different, and independently selected from the group consisting of hydrogen, aryl, hetero-aryl and halide; $R^5$ and $R^9$ are tertiary alkyl groups; $R^7$ and $R^{11}$ are same or different, and independently selected from the group consisting of hydrogen and tertiary alkyl group; and $R^3$ is independently selected from the group consisting of hydrogen, halogen, alkoxy, aryloxy, carboxylic and sulphonic.

In the final step, the Schiff base imine ligand of Formula IV obtained in the first step is chelated with the transition metal halide to obtain a transition metal based pro-catalyst of the present disclosure represented by Formula I.

In another embodiment, the process for preparing a transition metal based pro-catalyst of the present disclosure involves a step in which the Schiff base imine ligand of Formula (IV) is reacted with an alkali metal ion introducing agent to obtain an alkali metal salt of Schiff base imine ligand of Formula (V). The alkali metal salt formation reaction is schematically represented as below:

Formula (IV)

Formula (V)

wherein, the substituents $R^1$, $R^2$, $R^4$, $R^6$ $R^8$, $R^{10}$, $R^{12}$ $R^5$ and $R^9$, $R^7$, $R^{11}$ and $R^3$ have the meaning as defined above and $M_1$ is an alkali metal ion of alkali metal introducing agent.

The alkali metal salt of Schiff base imine ligand of Formula V is then chelated with the transition metal halide to obtain a transition metal based pro-catalyst of the present disclosure represented by Formula I.

The inventors of the present disclosure while conducting experiments found that the proportion of Schiff base imine ligand of Formula IV or the alkali metal salt of Schiff base imine ligand of Formula (V) to the transition metal halide plays vital role in deciding the type of pro-catalyst. For example, if the ratio Schiff base imine ligand of Formula IV or the alkali metal salt of Schiff base imine ligand of Formula (V) to transition metal halide is 1:1 then the product obtained is mono-chelated pro-catalyst represented by Formula (I).

The term "alkali metal salt formation" or "alkali metal ion introducing" or "alkali metal salt of" in the context of the present disclosure would mean a chemical reaction in which an alkali metal ion is attached to an organic molecule at hydroxyl oxygen position by substituting hydrogen ion of hydroxyl group.

Further, if the ratio of Schiff base imine ligand of Formula IV or Formula V to transition metal halide is 2:1 then the product obtained is a pro-catalyst comprising bis-chelated ligand.

Still further, if one has to prepare a pro-catalyst comprising tris-chelated ligand then the ratio of Schiff base imine ligand of Formula IV or formula V to transition metal halide is to be maintained at 3:1.

The alkali metal ion introducing agent selected for the formation of a salt of Schiff base imine ligand of Formula (IV) includes but is not limited to n-butyllithium, sodium hydride, lithium aminoalkoxide, Lithium diisopropylamide and combinations thereof.

In one embodiment, the substituted salicylaldehyde of Formula (IIIa) and the substituted salicylaldehyde of Formula (IIIb) used for obtaining the Schiff base imine ligand of Formula (IV) are same.

In another embodiment, the substituted salicylaldehyde of Formula (IIIa) and the substituted salicylaldehyde of Formula (IIIb) used for obtaining the Schiff base imine ligand of Formula (IV) are different.

The transition metal halide used in the process of the present disclosure includes but is not limited to Hafnium (Hf) halide, Manganese (Mn) halide, Iron (Fe) halide, Rhenium (Re) halide, Tungsten (W) halide, Niobium (Nb) halide, Tantalum (Ta) halide, Vanadium (V) halide, Titanium (Ti) halide and combinations thereof halide being selected from the group consisting of chloride, bromide and iodide. Titanium tetrachloride is preferably used as a transition metal halide for the purpose of the present disclosure.

In one embodiment the transition metal based pro-catalyst of the present disclosure can be used as a homogeneous pro-catalyst for polymerizing olefins.

The transition metal based pro-catalyst of the present disclosure may be converted into a heterogeneous catalyst by applying various known immobilization techniques involving use of inorganic oxides, organic supports, other inorganic supports, other macromolecular and polymeric supports like dendrimers and the like. The transition metal based pro-catalyst of the present disclosure and the support may be bonded to each other through bond which includes but is not limited to covalent bond, hydrogen bond, coordinate bond, coordinate covalent bond and physical bond.

In accordance with yet another aspect of the present disclosure there is provided a catalyst composition. The catalyst composition comprises a transition metal based pro-catalyst represented by Formula I, at least one alkyl aluminium co-catalyst, and at least one inert hydrocarbon liquid medium. To prepare the catalyst composition the pro-catalyst and the co-catalyst should be brought together in the inert hydrocarbon medium. However, due to the nature of the organic ligand of the pro-catalyst, the pro-catalyst cannot be dissolved in the inert hydrocarbon liquid medium directly. Therefore, the pro-catalyst is first dissolved in toluene like solvents which is then brought in contact with the suspension of the inert hydrocarbon liquid medium containing the alkyl aluminium co-catalyst.

The co-catalyst useful for the purpose of preparing the catalyst composition is alkyl aluminium compound selected from the group consisting of methylaluminoxane, polymethylaluminoxane, triethyl aluminium, isoprenyl aluminium, aluminium sesquichloride, tri-n-octyl aluminium, triisobutyl aluminium and combinations thereof. Particularly, polymethyl aluminoxane is used a co-catalyst.

The ratio of elemental aluminium to elemental titanium (Al/Ti) is critical for the polymerization reaction. Accordingly, the ratio of elemental aluminium to elemental titanium (Al/Ti) ranges from 50:1 to 1000:1, particularly, the ratio is in the range of 200:1 to 300:1.

Examples of the inert hydrocarbon liquid medium useful for the purpose of the present disclosure includes but is not limited to pentane, hexane, cyclohexane, methyl cyclohexane, heptane, octane, decane, toluene, isopentane and varsol. After series of experiments inventors of the present invention found that varsol is the most appropriate inert hydrocarbon liquid medium.

In accordance with yet another aspect of the present disclosure there is provided a process for polymerizing olefin by using a transition metal based pro-catalyst of the present disclosure represented by Formula I to obtain a dis-entangled ultra-high molecular weight polyolefin.

The transition metal based pro-catalyst of the present disclosure can be employed to carry out olefin polymerization either in the homopolymerization or co-polymerization mode optionally in the presence of suitable nano particle adjuvants like carbon nano tubes (single, multi walled and the like), silica and grapheme including all such new nano materials.

The polymerization of olefins is carried out under ambient conditions of temperature, pressure in the presence of liquid medium with higher boiling point, pro-catalyst of the present disclosure, and suitable aluminium alkyls as an activator.

In accordance to the present disclosure, in the first step, the transition metal based pro-catalyst is activated by treating with at least one alkyl aluminum compound co-catalyst under suitable conditions. The alkyl aluminum compound includes, but is not limited to methylaluminoxane, polymethylaluminoxane, triethyl aluminium, isoprenyl aluminium, aluminium sesquichloride, tri-n-octyl aluminium, triisobutyl aluminium and combinations thereof. In accordance with an exemplary embodiment of the present disclosure, the alkyl aluminum compound is polymethylaluminoxane. To sufficiently activate the transition metal based pro-catalyst the ratio of aluminium to titanium is maintained in the range of 50:1 and 1000:1. The activation of the pro-catalyst is achieved by the addition of the co-catalyst suspended in inert hydrocarbon liquid media into the pro-catalyst dissolved in toluene in a polymerization unit just before initiation of the polymerization process. The inert hydrocarbon used as a liquid medium during the activation of the catalyst is selected from the group which includes but is not limited to pentane, hexane, cyclohexane, methyl cyclohexane, heptane, octane, decane, toluene, isopentane, varsol and mixtures thereof.

Typically, an inert hydrocarbon used as a liquid medium during the activation of the catalyst is varsol.

The method step of activating catalyst is carried out at temperature ranges from 10° C. to 30° C. and under inert atmosphere.

In the second step, olefin monomer having carbon atom in the range of 2 to 18 is added to the activated catalyst to obtain a reaction mixture. The reaction mixture is then subjected to polymerization at a temperature ranging from −5° C. to 70° C. and at a pressure ranging from 0.1 to 11 bars for a time period ranging from 1 hour to 10 hours to obtain a disentangled ultra-high molecular weight polyolefin. The molecular weight of the obtained polyolefin ranges from 1 million g/mole to 6 million g/mole. By suitably varying the process conditions during polymerization, as is known to persons well versed in the area of olefin polymerization, it is possible to further increase the molecular weight of the polymer produced using this catalyst composition. The highly disentangled nature of the polyolefin prepared using the catalyst composition of the present disclosure is associated with the structure and nature of the ligand present in the pro-catalyst. The ligand based on aromatic diamine and substituted salicylaldehyde controls the electronic and geometric environment around the central titanium in the catalyst in such a manner that it produces disentangled ultra-high molecular weight polyolefin. The pro-catalyst of the present disclosure also contributes in controlling polymerization kinetics. Further, it was observed that the co-catalyst interacts with the pro-catalyst of the present disclosure to form a cationic complex which regulates molecular weight of the resulting polyolefin and terminates the polymerization reaction at required stage.

In an exemplary embodiment of the present disclosure the polymerization of ethylene was carried out using the transition metal based pro-catalyst of the present disclosure. The resulting polyethylene was highly disentangled. The disentanglement was observed by conducting tests such as sheet formation below melt temperature under pressure. It was further observed that the sheet could be drawn into very high strength films, tapes and fibres of more than 1 GPa. The polyethylene obtained was also molded into different forms having high strength.

The polyethylene obtained using the transition metal based catalyst of Formula (I) exhibits the following properties:

bulk density ranging from 0.05 to 0.1 g/cc, crystallinity as determined using DSC and XRD is 90% to 99%, molecular weight in the range of 1 million g/mole to 6 million g/mole, and intrinsic viscosity in the range of 10 dl/g to 32 dl/g, fibrous and porous morphology.

The invention shall now be described with the following non-limiting example/s.

EXAMPLES

Example 1

Step A

Preparation of Schiff Base Imine Ligand (C)

All operations were carried out in nitrogen atmosphere. m-phenylene diamine (1.08 g, 10 mmol), 3-tert butyl salicylaldehyde (3.42 mL, 20 mmol) and p-toluene sulfonic acid (10 mg) were dissolved in anhydrous toluene (50 mL) and the mixture was stirred at 110° C. under nitrogen atmosphere for 5 hrs. The resulting mixture was concentrated in vacuum to obtain crude Schiff base imine ligand (C) as dark brown solid. The crude Schiff base imine ligand (C) was purified by column chromatography on silica gel using n-hexane/ethyl acetate (100:1) as eluent to give pure product, Schiff base imine ligand (C) as bright orange solid (3.6 g; yield 85%).

Schiff base imine ligand (C)

Step B

Lithiation of Schiff Base Imine Ligand Followed by Chelation with Titanium Tetrachloride Schiff base imine ligand
(C)

1:1 (Ligand: TiCl₄)
Or Mono chelate
(A)

All operations were carried out in nitrogen atmosphere. Schiff base imine ligand (C) (1.0 g, 2.33 mmol) was dissolved in dry diethyl ether (100 mL) under gentle agitation and the resulting mixture was, cooled to −78° C. using a dry ice, acetone bath. To the mixture, 1.52 M of n-butyllithium/n-hexane solution (3.2 mL, 4.94 mmol) was added drop wise over a period of 10-15 mins. The solution was allowed to warm to room temperature and was stirred for 3 hrs to complete the lithiation reaction. The resulting reaction mixture was again cooled to −78° C. and TiCl₄ (0.25 mL, 2.32 mmol) was added to it drop wise. The mixture was allowed to warm to room temperature and was stirred for 15 to 18 hrs to obtain a dark red brown solution. The solution was concentrated in vacuum to obtain crude (A) as dark brown solid. 50.0 mL portion of dichloromethane was added to crude (A) and stirred for 5 min, and then filtered through a medium porosity G-2 sinter funnel.

This step was repeated twice (50 mL dichloromethane—each time) to remove all solid impurities from the crude (A). The organic filtrate (DCM extract) was combined and dried under vacuum to obtain brown solids. The solids were then washed with n-hexane/di ethyl ether (95:5) solution (3 times, each time 20 mL solution), followed by washing with n-hexane (20 mL) to give pure (mono chelate) (A) as brownish red solid (1.3 g, yield 97%).

Similarly above synthetic procedure can result in bis chelate when ligand: TiCl₄ molar ratio is 2:1 and tris chelate when ligand: TiCl₄ molar ratio is 3:1.

Characterization Data a. For Formula I Wherein Substituents are as Follows (A): $R^1$, $R^2$, $R^3$, $R^4$, $R^6$, $R^7$, $R^8$, $R^{10}$, $R^{11}$ and $R^{12}$ being hydrogen; $R^5$ and $R^9$ being tertiary butyl groups; M is Titanium (Ti); X is Cl and n is an integer 2

Molecular formula of pro-catalyst: $C_{28}H_{30}Cl_2N_2O_2Ti$

Elemental analysis: C: 61.35% (Theoretical: 61.67%), H: 5.31% (Theoretical: 5.54%), Cl: 13.52% (Theoretical: 13:00%), N: 5.09% (Theoretical: 5.14%), Ti: 8.54% (Theoretical: 8.78%).

The mass spectrum (FIG. 3) taken in EI (electron ionization) mode shows peak at 617.53 m/z which corresponds to an adduct of molecular ion (mass 545.46) with pentane (mass 72). Pentane gas is used for mass spectra analysis in EI mode. In CI (chemical ionization) mode of analysis (FIG. 4), only ligand peak at 428.56 m/z appears as in CI mode the catalyst gets fragmented to its stable ligand part.

Figure 3:
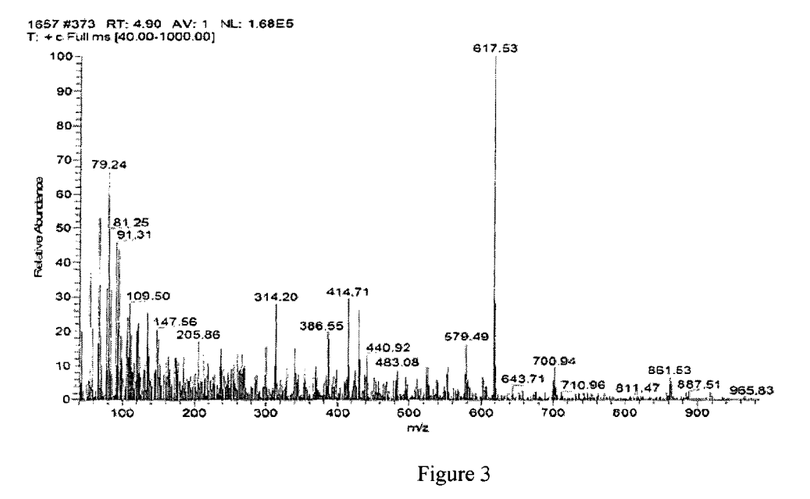
FIG. 3—illustrates mass spectrum taken in EI (electron ionization) mode for the pro-catalyst (A)
Figure 4:
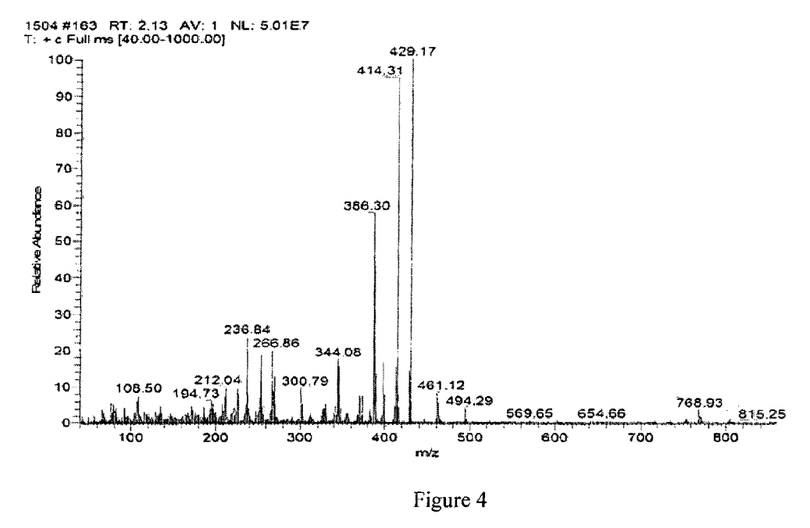
FIG. 4—illustrates mass spectrum taken in CI (chemical ionization) mode for the pro-catalyst (A)

These types of catalysts are well known to form cationic complexes with Lewis acids. Hence getting the correct mass spectrum for such sensitive catalysts is pretty difficult using EI and CI mode. Even trace moisture can generate HCl from the Ti chelates to form adducts with the cationic counterpart of the catalyst moiety. None the less, indirect evidence for the presence of Ti and Cl from elemental analysis, besides the dark red brown color, is adequate to arrive at the molecular/empirical formula proposed.

B. For Formula I Wherein Substituents are as Follows (B) $R^1$, $R^2$, $R^3$, $R^4$, $R^6$, $R^8$, $R^{10}$ and $R^{12}$ being hydrogen; $R^5$, $R^9$, $R^7$ and $R^{11}$ being tertiary butyl groups; M is Titanium (Ti); X is Cl and n is an integer 2

Molecular formula of pro-catalyst: $C_{36}H_{46}Cl_2N_2O_2Ti$

Elemental analysis: C: 65.54% (Theoretical: 65.76%), H: 7.11% (Theoretical: 7.05%), Cl: 11.12% (Theoretical: 10.78%), N: 4.15% (Theoretical: 4.26%), Ti: 7.15% (Theoretical: 7.28%).

Figure 5:
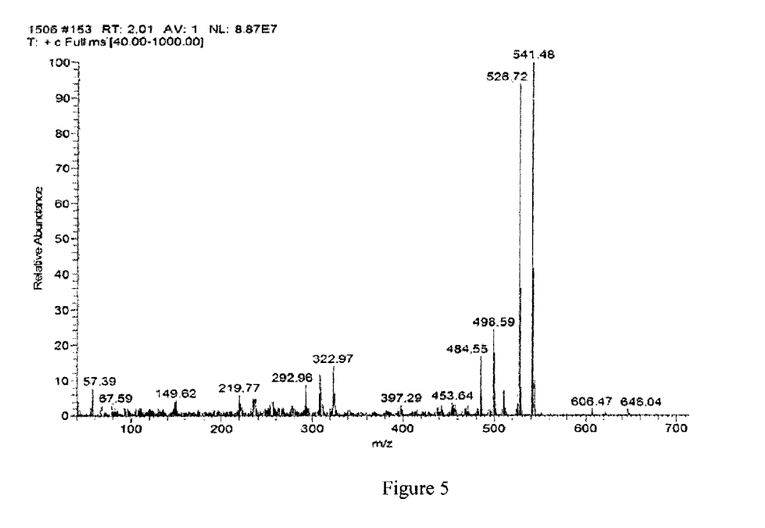
FIG. 5—illustrates mass spectrum taken in EI (electron ionization) mode for the pro-catalyst (B)

The mass spectrum (FIG. 5), taken in EI (electron ionization) mode shows peak at 541.48 m/z which corresponds to ligand part (mass 540.1) of claimed catalyst. During analysis in EI mode the catalyst gets fragmented to its stable ligand part. The other relevant analytical data related to Ti and Cl content substantiates the proposed molecular formula for the said catalyst. The said pro-catalyst also polymerizes ethylene effectively, which will not be the case had it been only the ligand.

c. Comparison of the Catalyst Comprising Pro-Catalyst (A) with the Prior Art Catalyst in Terms of Cost, Toxicity, Reaction Kinetic Profile, Reactor Fouling, Polymer Characteristics Etc. To Show that the Catalyst Comprising Pro-Catalyst (A) is Efficient than the Prior Art Catalysts The prior art catalyst which can effectively produce Dis-entangled ultrahigh molecular weight polyethylene contains pentafluoro aniline moiety in its ligand part. Unlike the prior art catalyst, the transition metal base catalyst comprising pro-catalyst (A) does not have any pentafluoro aniline moiety which makes this pro-catalyst more environmental friendly compared to existing prior art catalyst.

The transition metal catalyst comprising pro-catalyst (A) is very economical in comparison to the prior art catalyst because of the absence of costly pentafluoro aniline moiety.

Figure 1:
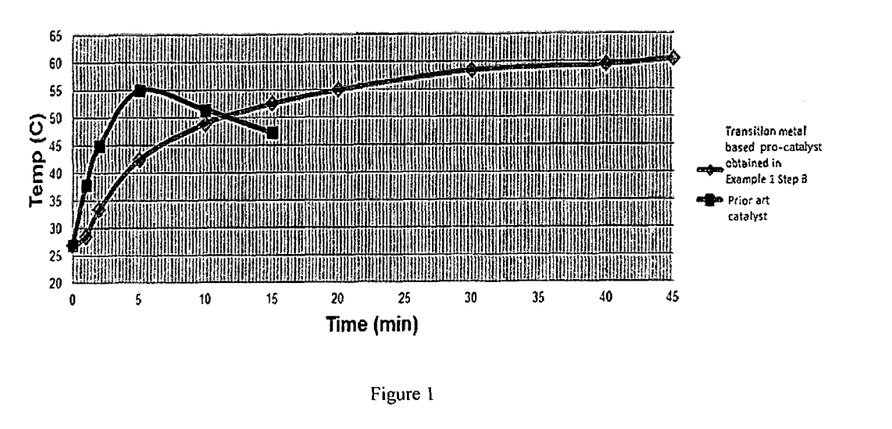
FIG. 1—illustrates the comparative kinetic profile of the polymerization reaction using the transition metal based pro-catalyst (A) with that of the prior art catalyst.

The prior art catalyst shows rapid reaction kinetic profile (as shown in graph in FIG. 1) where polymerization reaction temperature increases from room temperature to 55° C. on its own within 4-5 min and can result in fouling of polymerization reactor, if proper heat drainage is not done using a cryostat. On the other hand, under identical polymerization conditions, the transition metal catalyst comprising pro-catalyst (A) shows milder reaction kinetics (as shown in graph below) where polymerization reaction temperature increases slowly from room temperature to maximum temperature over a time period of 35-40 min. Since catalyst comprising pro-catalyst (A) shows controlled reaction kinetics, it prevents fouling of reactor even at temperatures around 60° C. because of slow, steady and uniform polymer formation preventing agglomeration even in the absence of a cryostat.

In addition to having rapid kinetic profile, the prior art catalyst also exhibits living ethylene polymerization nature where molecular weight of polymer increases rapidly over time. As a result, it shows difficulty to control the molecular weight of the polymer along with desired yield of polymer, especially in the lower molecular weight range of 1 to 6 million g/mole. The transition metal catalyst comprising pro-catalyst (A) shows controlled and milder reaction kinetics, which is beneficial for better process control, especially for achieving molecular weight in the range of 1 to 6 million g/mole along with improved polymer yield. MW ranging from 1 to 6 M g/mole is ideal for ease of polymer processing and hence the transition metal catalyst comprising pro-catalyst (A) is efficient in terms of productivity and process to achieve desired molecular weights.

Figure 2:
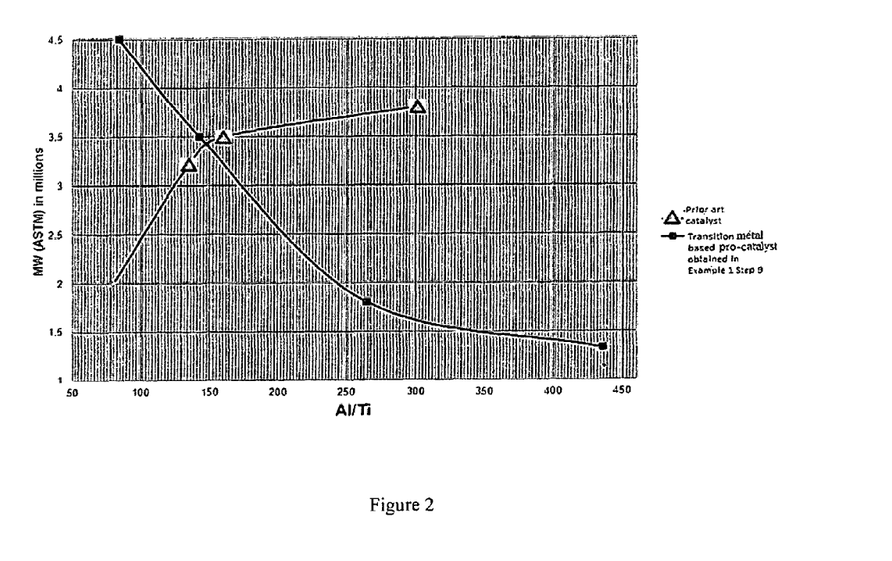
FIG. 2—illustrates the effect of the ratio of co-catalyst/catalyst (Al/Ti) on the polymerization profiles using the transition metal based pro-catalyst (A) and the prior art catalyst.

The graph presented in FIG. 2, illustrates the effect of co-catalyst/catalyst (Al/Ti) ratio on the polymerization profiles for both the catalysts. Increasing the Al/Ti ratio for the transition metal catalyst comprising pro-catalyst (A) results in lowering of molecular weight since the co-catalyst also functions as a chain terminating agent regulating the mol·wt., besides activating the catalyst. In the case of prior art catalyst the MW increases with Al/Ti ratio and also due to its living nature. That is why the transition metal catalyst comprising pro-catalyst (A) shows better control of MW in the region of 1 to 6 milliong/mole.

The transition metal catalyst comprising pro-catalyst (A) is capable of achieving desired molecular weight of 1 to 6 million g/mole with enhanced productivity, in comparison to the prior art catalyst. See table 1 below:

TABLE 1

Performance of the transition metal based catalyst comprising pro-catalyst A in the preparation of Dis-entangled ultrahigh-molecular weight polyethylene in comparison to that of prior art catalyst

| Catalyst | *Al/Ti | Yield (g) | Yield (g/g cat) | Time (m) | MW in million (g/mol) on ASTM scale |
|---|---|---|---|---|---|
| Catalyst comprising pro-catalyst A | 222 | 340 | 850 | 180 | 2 |
| Catalyst comprising pro-catalyst A | 222 | 440 | 1100 | 180 | 1.9 |
| Catalyst comprising pro-catalyst A | 208 | 460 | 1050 | 180 | 2.72 |
| Prior art catalyst | 220 | 430 | 843 | 45 | 6.8 |
| Prior art catalyst | 220 | 330 | 647 | 45 | 6.9 |
| Prior art catalyst | 257 | 440 | 863 | 45 | 7.1 |

Al is from PMAO which is used as co-catalyst. Polymerization is done in varsol as medium with ethylene pressure of 2.5 bars under 500 rpm agitation. The reactor is of SS316 metal and 19 L capacity.

The performance characteristics of the transition metal based catalyst comprising pro-catalyst A (through the lithiation and non lithiation routes) in the preparation of Dis-entangles ultrahigh molecular weight polyethylene under different process conditions are given below (Table 2)—exemplifying the results. A typical polymerization reaction was carried out in the 1 L Buchi Polyclave Glass Reactor using 500 mL of the polymerization medium admixed with PMAO as co-catalyst; followed by addition of catalyst and ethylene at ambient temperature (26-28° C.). Agitation was ~500 rpm.

TABLE 2

| Catalyst | Catalyst (mg) | C2 pressure (bar) | Al/Ti | Time (min) | Yield (g/g catalyst) | MW in million (g/mol) on ASTM scale | Polymerization medium |
|---|---|---|---|---|---|---|---|
| Catalyst comprising pro-catalyst A-Prepared via lithiation route | 18 | 2.5 | 84 | 60 | 543 | 4.5 | Varsol |
|  | 18 | 2.5 | 141 | 60 | 1315 | 3.5 |  |
|  | 18 | 2.5 | 141 | 180 | 1327 | 5.9 |  |
|  | 18 | 2.5 | 248 | 45 | 1554 | 1.3 |  |
|  | 18 | 2.5 | 248 | 60 | 1768 | 1.8 |  |
|  | 18 | 2.5 | 248 | 120 | 2071 | 2.9 |  |
| Catalyst comprising pro-catalyst A-Prepared via lithiation route | 16.5 | 2.5 | 215 | 120 | 4200 | 3.9 | Varsol |
|  | 16.0 | 2.5 | 215 | 120 | 4400 | 3.8 |  |
|  | 17.3 | 2.5 | 215 | 120 | 4300 | 4.0 |  |
|  | 18.0 | 2.5 | 215 | 120 | 4400 | 3.9 |  |
|  | 8.0 | 2.5 | 215 | 120 | 3900 | 5.7 |  |
|  | 7.5 | 2.5 | 215 | 120 | 4100 | 5.5 |  |
| Catalyst comprising pro-catalyst A-Prepared | 18 | 2.5 | 215 | 180 | 5000 | 4.2 | Varsol |
|  | 18 | 5.0 | 215 | 180 | 5700 | 4.2 |  |
|  | 14 | 5.0 | 215 | 180 | 6700 | 5.3 |  |
|  | 12 | 5.0 | 215 | 180 | 5400 | 5.5 |  |

TABLE 2-continued

| Catalyst | Catalyst (mg) | C2 pressure (bar) | Al/Ti | Time (min) | Yield (g/g catalyst) | MW in million (g/mol) on ASTM scale | Polymerization medium |
|---|---|---|---|---|---|---|---|
| via lithiation route | 10 | 7.0 | 215 | 180 | 5400 | 5.8 | |
| | 18 | 0.5-1.0 | 215 | 360 | 5300 | 7.1 (polymerization done at 15° C.) | |
| | 18 | 0.5-1.0 | 215 | 180 | 5200 | 6.2 (polymerization done at 15° C.) | |
| Catalyst comprising pro-catalyst A-Prepared via lithiation route | 18 | 2.5 | 215 | 180 | 4200 | 4.8 | Toluene |
| Catalyst comprising pro-catalyst A-Prepared via lithiation route | 18 | 2.5 | 215 | 180 | 4400 | 4.7 (Hexane as polymerization medium) | Hexane |
| Catalyst comprising pro-catalyst A-Prepared via non-lithiation route | 16.5 | 2.5 | 215 | 180 | 4300 | 4.1 | Varsol |
| | 16.0 | 2.5 | 215 | 180 | 4100 | 4.0 | |
| | 17.5 | 2.5 | 215 | 180 | 4400 | 4.5 | |
| | 18.5 | 2.5 | 215 | 180 | 4600 | 4.6 | |
| Catalyst comprising pro-catalyst B-Prepared via lithiation route | 20.4 | 2.5 | 215 | 180 | 3800 | 3.9 | Varsol |
| | 16.0 | 2.5 | 215 | 180 | 3700 | 4.0 | |
| Catalyst comprising pro-catalyst B-Prepared via non lithiation route | 20.7 | 2.5 | 215 | 180 | 3850 | 3.5 | Varsol |
| | 18 | 2.5 | 215 | 180 | 3500 | 3.7 | |

Most of the polymerization reactions exhibited a very controlled kinetic profile and were performed at a temperature in the range of 45-48° C.

The polyethylene obtained from all the above experiments had a fibrous and porous morphology, bulk density ranging from 0.05-0.1 g/cc with high crystallinity (Obtained from DSC and XRD).

Figure 6:
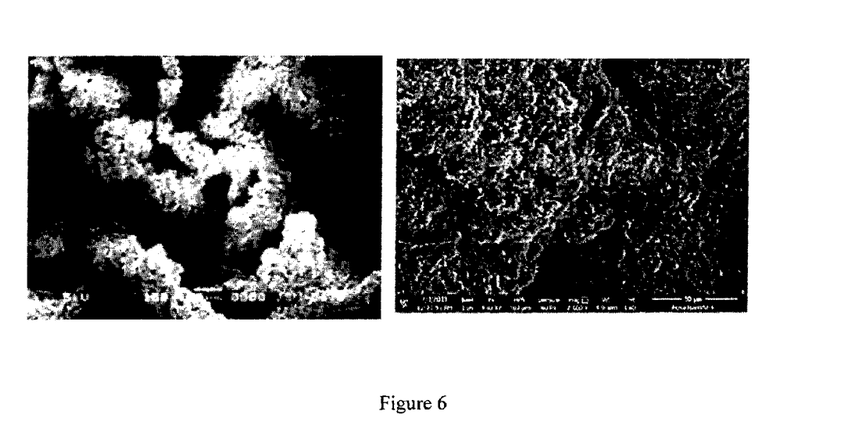
FIG. 6—illustrates SEM image of one of the representative polymer obtained using the pro-catalyst of the present disclosure.

The SEM image of one the representative polymer sample exhibiting the fibrous and porous morphology is depicted in FIG. 6.

Figure 7:
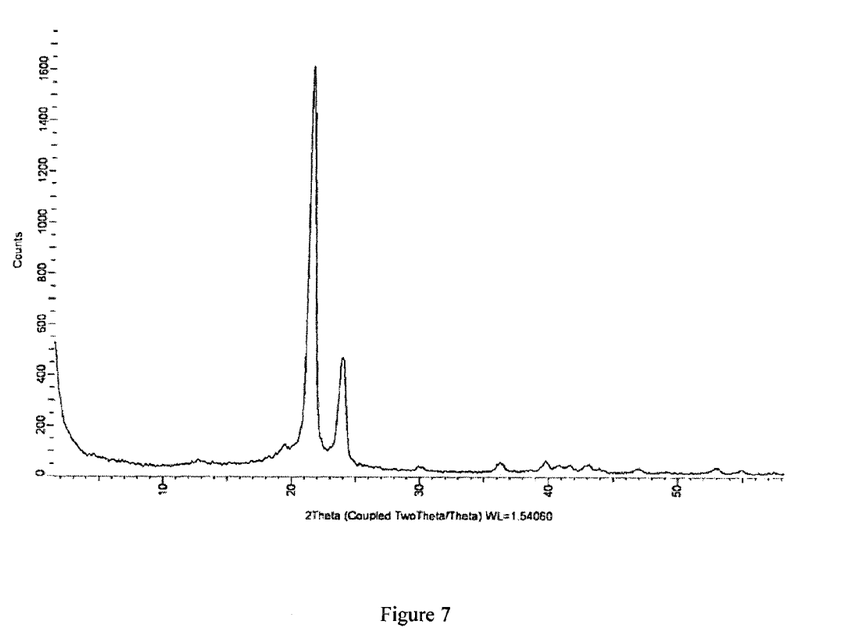
FIG. 7—illustrates XRD of one of the representative polymer obtained using the pro-catalyst of the present disclosure.

The XRD of one representative polymer sample depicting the highly crystalline nature is shown in FIG. 7.

The DUHMPE obtained using the transition metal catalyst comprising pro-catalyst (A) is identical in all aspects (low bulk density ranging from 0.05 to 0.10 g/cc; enhanced crystallinity (95-99%) as seen from XRD, ability to stretch below melt temperature and fibrous/porous morphology) like DUHMWPE obtained by prior art catalyst.

Technical Advantages and Economic Significance

A novel transition metal based pro-catalyst of the present disclosure effectively controls polymerization reaction kinetics and regulates molecular weight more efficiently, thereby making the process of polymerization economical and environment friendly.

The use of transition metal based pro-catalyst of the present disclosure prevents fouling of the polymerization unit unlike the polymerization processes employing prior art catalyst/s.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A transition metal based pro-catalyst represented by Formula I:

Formula I wherein, $R^1$, $R^2$, $R^4$, $R^6$ $R^8$, $R^{10}$ and $R^{12}$ are the same or different, and are independently selected from the group consisting of hydrogen, aryl, hetero-aryl and halide;

$R^5$ and $R^9$ are tertiary alkyl groups;

$R^7$ and $R^{11}$ are the same or different, and are independently selected from the group consisting of hydrogen and tertiary alkyl group;

$R^3$ is independently selected from the group consisting of hydrogen, halogen, alkoxy, aryloxy, carboxylic and sulphonic;

M is a transition metal selected from the group consisting of hafnium (Hf), manganese (Mn), iron (Fe) rhenium (Re), tungsten (W), niobium (Nb), tantalum (Ta), vanadium (V) and titanium (Ti);

X is a halide selected from the group consisting of Cl, Br and I; and n is an integer 2.

2. The transition metal based pro-catalyst as claimed in claim 1, wherein the pro-catalyst consists of a set of substituents selected from the group consisting of:

i. $R^1$, $R^2$, $R^3$, $R^4$, $R^6$, $R^7$, $R^8$, $R^{10}$, $R^{11}$ and $R^{12}$ being hydrogen; $R^5$ and $R^9$ being tertiary butyl groups; M is titanium (Ti); X is Cl and n is an integer 2; and ii. $R^1$, $R^2$, $R^3$, $R^4$, $R^6$, $R^8$, $R^{10}$ and $R^{12}$ being hydrogen; $R^5$, $R^9$, $R^7$ and $R^{11}$ being tertiary butyl groups; M is titanium (Ti); X is Cl and n is an integer 2.

3. A process for preparing the transition metal based pro-catalyst as claimed in claim 1, said process comprising:

i. reacting an aromatic diamine of Formula (II) and at least one substituted salicylaldehyde of Formula (IIIa/IIIb) to obtain a Schiff base imine ligand of Formula (IV),

Formula (II)

Formula (IIIa)

Formula (IIIb)

Formula (IV)

wherein, $R^1$, $R^2$, $R^4$, $R^6$ $R^8$, $R^{10}$ and $R^{12}$ are the same or different, and are independently selected from the group consisting of hydrogen, aryl, hetero-aryl and halide;

$R^5$ and $R^9$ are tertiary alkyl groups;

$R^7$ and $R^{11}$ are same or different, and are independently selected from the group consisting of hydrogen and tertiary alkyl group;

$R^3$ is independently selected from the group consisting of hydrogen, halogen, alkoxy, aryloxy, carboxylic and sulphonic, and ii. optionally, introducing an alkali metal ion in the Schiff base imine ligand of Formula (IV) using an alkali metal ion introducing agent to obtain an alkali metal salt of Schiff base imine ligand of Formula (V), Formula (IV)

Formula (V)

wherein, $R^1$, $R^2$, $R^4$, $R^6$ $R^8$, $R^{10}$ and $R^{12}$ are the same or different, and are independently selected from the group consisting of hydrogen, aryl, hetero-aryl and halide;

$R^5$ and $R^9$ are tertiary alkyl groups;

$R^7$ and $R^{11}$ are the same or different, and are independently selected from the group consisting of hydrogen and tertiary alkyl group;

$R^3$ is independently selected from the group consisting of hydrogen, halogen, alkoxy, aryloxy, carboxylic and sulphonic; and $M_1$ is an alkali metal ion of alkali metal ion introducing agent, and iii. chelating the Schiff base imine ligand of Formula IV or alkali metal salt of Schiff base imine ligand of Formula (V) with a transition metal halide to obtain the transition metal based pro-catalyst represented by Formula I:

Formula I wherein, $R^1$, $R^2$, $R^4$, $R^6$ $R^8$, $R^{10}$ and $R^{12}$ are the same or different, and are independently selected from the group consisting of hydrogen, aryl, hetero-aryl and halide;

$R^5$ and $R^9$ are tertiary alkyl groups;

$R^7$ and $R^{11}$ are the same or different, and are independently selected from the group consisting of hydrogen and tertiary alkyl group;

$R^3$ is independently selected from the group consisting of hydrogen, halogen, alkoxy, aryloxy, carboxylic and sulphonic;

M is a transition metal selected from the group consisting of hafnium (Hf), manganese (Mn), iron (Fe), rhenium (Re), tungsten (W), niobium (Nb), tantalum (Ta), vanadium (V) and titanium (Ti);

X is a halide selected from the group consisting of Cl, Br and I; and n is an integer 2.

4. The process as claimed in claim 3, wherein the ratio of Schiff base imine ligand of Formula IV or alkali metal salt of Schiff base imine ligand of Formula (V) to the transition metal halide is 1:1.

5. The process as claimed in claim 3, wherein the step (i) is carried out in the presence of at least one compound selected from the group consisting of p-toluene sulfonic acid and sulphuric acid in at least one liquid medium selected from the group consisting of toluene, xylene, hexane, methanol and ethanol at a temperature ranging from 40° C. to the boiling point of the liquid medium.

6. The process as claimed in claim 3, wherein the substituted salicylaldehyde is at least one compound selected from the group consisting of 3-tert-butyl salicylaldehyde and 3,5-di-tert-butyl salicylaldehyde.

7. The process as claimed in claim 3, wherein the substituted salicylaldehyde of Formula (Ma) and the substituted salicylaldehyde of Formula (IIIb) are the same or different.

8. The process as claimed in claim 3, wherein the pro-catalyst consists of a set of substituents selected from the group consisting of:

i. $R^1$, $R^2$, $R^3$, $R^4$, $R^6$, $R^7$, $R^8$, $R^{10}$, $R^{11}$ and $R^{12}$ being hydrogen; $R^5$ and $R^9$ being tertiary butyl groups; M is titanium (Ti); X is Cl; and n is an integer 2; and ii. $R^1$, $R^2$, $R^3$, $R^4$, $R^6$, $R^8$, $R^{10}$ and $R^{12}$ being hydrogen; $R^5$, $R^9$, $R^7$ and $R^{11}$ being tertiary butyl groups; M is titanium (Ti); X is Cl; and n is an integer 2.

9. The process as claimed in claim 3, wherein the alkali metal ion introducing agent is at least one selected form the group consisting of n-butyllithium, sodium hydride, lithium aminoalkoxide and lithium diisopropylamide.

10. A catalyst composition comprising:
i. a transition metal based pro-catalyst represented by Formula I;

Formula I wherein,
- $R^1$, $R^2$, $R^4$, $R^6$ $R^8$, $R^{10}$ and $R^{12}$ are the same or different, and are independently selected from the group consisting of hydrogen, aryl, hetero-aryl and halide;
- $R^5$ and $R^9$ are tertiary alkyl groups;
- $R^7$ and $R^{11}$ are same or different, and are independently selected from the group consisting of hydrogen and tertiary alkyl group;
- $R^3$ is independently selected from the group consisting of hydrogen, halogen, alkoxy, aryloxy, carboxylic and sulphonic;
- M is a transition metal selected from the group consisting of hafnium (Hf), manganese (Mn), iron (Fe), rhenium (Re), tungsten (W), niobium (Nb), tantalum (Ta), vanadium (V) and titanium (Ti);
- X is a halide selected from the group consisting of Cl, Br and I; and
- n is an integer 2, ii. at least one alkyl aluminium co-catalyst; and
iii. at least one inert hydrocarbon liquid medium.

11. The catalyst composition as claimed in claim 10, wherein the alkyl aluminium co-catalyst is at least one compound selected from the group consisting of methylaluminoxane, poly-methylaluminoxane, triethyl aluminium, isoprenyl aluminium, aluminium sesquichloride, tri-n-octyl aluminium and triisobutyl aluminium.

12. The catalyst composition as claimed in claim 10, wherein the co-catalyst is polymethyl aluminoxane.

13. The catalyst composition as claimed in claim 10, wherein the ratio of elemental aluminium to elemental titanium (Al/Ti) is in the range of 50:1 to 1000:1.

14. The catalyst composition as claimed in claim 10, wherein the inert hydrocarbon liquid medium is at least one selected from the group consisting of pentane, hexane, cyclohexane, methyl cyclohexane, heptane, octane, decane, toluene, isopentane and, mineral spirit.

15. The catalyst composition as claimed in claim 10, wherein the ratio of elemental aluminium to elemental titanium (Al/Ti) is in the range of 200:1 to 300:1 and the inert hydrocarbon liquid medium is mineral spirit.

16. A process for polymerizing olefin, said process comprising:
i. mixing the transition metal based pro-catalyst of claim 1 and at least one co-catalyst in a proportion wherein the ratio of elemental aluminium to elemental titanium ranges from 50:1 to 1000:1, in the presence of at least one inert hydrocarbon liquid medium at a temperature ranging from 10° C. to 30° C. to obtain an activated catalyst composition,
ii. adding at least one olefin monomer to the activated catalyst composition to obtain a reaction mixture, and
iii. subjecting the reaction mixture to polymerization at a temperature ranging from −5° C. to 70° C., and a pressure ranging from 0.1 to 11 bar for a time period ranging from 1 hour to 10 hours to obtain the polymerized olefin.

17. The process for polymerizing olefin as claimed in claim 16, wherein the inert hydrocarbon liquid medium is at least one selected from the group consisting of pentane, hexane, cyclohexane, methyl cyclohexane, heptane, octane, decane, toluene, isopentane, and mineral spirit.

18. The process for polymerizing olefin as claimed in claim 16, wherein the olefin monomer is ethylene and the inert hydrocarbon liquid medium is mineral spirit.

* * * * *